(12) United States Patent
Ideker et al.

(10) Patent No.: US 9,561,383 B2
(45) Date of Patent: Feb. 7, 2017

(54) IMPLANTABLE CARDIOVERTER DEFIBRILLATOR (ICD), SUBCUTANEOUS IMPLANTABLE CARDIOVERTER DEFIBRILLATOR (SICD), AND WAVEFORM ENERGY CONTROL SYSTEMS

(71) Applicant: RUSE TECHNOLOGIES, LLC, Brookhaven, GA (US)

(72) Inventors: Raymond E. Ideker, Birmingham, AL (US); Richard B. Ruse, Brookhaven, GA (US); Scott Bohanan, Statesboro, GA (US)

(73) Assignee: Ruse Technologies, LLC, Brookhaven, GA (US)

( * ) Notice: Subject to any disclaimer, the term of this patent is extended or adjusted under 35 U.S.C. 154(b) by 0 days.

(21) Appl. No.: 14/881,887

(22) Filed: Oct. 13, 2015

(65) Prior Publication Data
US 2016/0101293 A1   Apr. 14, 2016

Related U.S. Application Data

(60) Provisional application No. 62/062,302, filed on Oct. 10, 2014, provisional application No. 62/062,319, filed on Oct. 10, 2014, provisional application No. 62/066,399, filed on Oct. 21, 2014, provisional application No. 62/067,588, filed on Oct. 23, 2014, provisional application No. 62/210,520, filed on Aug. 27, 2015.

(51) Int. Cl.
*A61N 1/39* (2006.01)

(52) U.S. Cl.
CPC .......... *A61N 1/3962* (2013.01); *A61N 1/3906* (2013.01); *A61N 1/3937* (2013.01); *A61N 1/3987* (2013.01); *A61N 1/395* (2013.01)

(58) Field of Classification Search
None
See application file for complete search history.

(56) References Cited

U.S. PATENT DOCUMENTS

| | | | |
|---|---|---|---|
| 4,870,341 A * | 9/1989 | Pihl | A61N 1/3931 324/600 |
| 5,772,692 A * | 6/1998 | Armstrong | A61N 1/3712 607/11 |
| 6,438,418 B1 | 8/2002 | Swerdlow et al. | |
| 7,920,918 B2 | 4/2011 | Ideker | |
| 7,983,748 B2 | 7/2011 | Ruse | |

(Continued)

*Primary Examiner* — Kennedy Schaetzle
(74) *Attorney, Agent, or Firm* — William H. Dippert; Laurence A. Greenberg; Werner H. Stemer

(57) ABSTRACT

Cardiac defibrillation or cardioversion waveform energy control systems employ transvenous ICDs, subcutaneous SICDs, or pacemakers for treating cardiac conditions. The systems comprise differentially driven amplifier circuit operational modes to control the delivery of pacing, anti-tachycardia pacing, defibrillation, and/or cardioversion electrical shocks, wherein the pacing, anti-tachycardia pacing, and shock waveforms employ constant current, constant voltage, or constant energy. Biphasic arbitrary shock waveforms deliver increasing energy with increasing time as represented by phase 1 ascending ramp, ascending exponential, ascending chopped, ascending stepped, ascending curved, square, or rectilinear and/or any combination of geometric shaped ascending arbitrary waveforms or any BTE waveform.

15 Claims, 12 Drawing Sheets

(56) References Cited

U.S. PATENT DOCUMENTS

| | | | | |
|---|---|---|---|---|
| 2003/0125773 A1* | 7/2003 | Havel | ............... | A61N 1/3906 607/7 |
| 2005/0107834 A1 | 5/2005 | Freeman et al. | | |
| 2009/0157130 A1 | 6/2009 | Ideker et al. | | |
| 2010/0217344 A1* | 8/2010 | Carranza | ............. | A61N 1/3975 607/5 |
| 2012/0179218 A1 | 7/2012 | Moulder | | |
| 2013/0296974 A1 | 11/2013 | Wanasek | | |

* cited by examiner

IMPLANTABLE CARDIOVERTER DEFIBRILLATOR (ICD), SUBCUTANEOUS IMPLANTABLE CARDIOVERTER DEFIBRILLATOR (SICD), AND WAVEFORM ENERGY CONTROL SYSTEMS

CROSS-REFERENCE TO RELATED APPLICATIONS

This patent is based upon and claims the benefit of the filing date of commonly assigned U.S. Provisional Patent Application Ser. No. 62/062,302, filed Oct. 10, 2014; commonly assigned U.S. Provisional Patent Application Ser. No. 62/062,319, filed Oct. 10, 2014; commonly assigned U.S. Provisional Patent Application Ser. No. 62/066,399, filed Oct. 21, 2014; commonly assigned U.S. Provisional Patent Application Ser. No. 62/067,588, filed Oct. 23, 2014; and commonly assigned U.S. Provisional Patent Application Ser. No. 62/210,520, filed Aug. 27, 2015, each of which applications is incorporated herein in its entirety.

FIELD OF THE INVENTION

This invention is directed to the electrical management of cardiac arrhythmias or abnormal heart rhythms that occur in the electrical systems of the atrial or ventricular chambers of the human heart. More particularly, the invention is directed to subcutaneous implantable defibrillators and waveform energy control management.

BACKGROUND OF THE INVENTION

Ventricular fibrillation (VF) is a cause of cardiac arrest and sudden cardiac death. During VF, the ventricular muscle contracts in a much less organized pattern than during normal sinus rhythm, so the ventricles fail to pump blood into the arteries and systemic circulation. VF is a sudden, lethal arrhythmia responsible for many deaths in the Western world, mostly brought on by ischemic heart disease. VF, which occurs in approximately 2 out of 10,000 people per year, is a medical emergency. If the arrhythmia continues for more than a few seconds, blood circulation will cease as evidenced by lack of pulse, blood pressure and respiration, and death will occur.

Despite much work, the underlying nature of VF is not completely understood. Most episodes of VF occur in diseased hearts, but other episodes occur in structurally normal hearts. Much work still has to be done to understand the mechanisms of VF.

Ventricular tachycardia (VT) is a tachyarrhythmia originating from an ectopic ventricular region, characterized by a rate typically greater than 100 beats per minute and wide QRS complexes. VT may be monomorphic, i.e., originating from a single repeating pathway with identical QRS complexes, or polymorphic, i.e., following changing pathways, with varying QRS complexes. Non-sustained VT is defined as an episode of tachycardia of less than 30 seconds duration; longer runs are considered sustained VT.

No absolute ECG criteria exist for establishing the presence of VT. However, several factors suggest VT, including the following: rate greater than 100 beats per minute (usually 150-200), wide QRS complexes (>120 ms), presence of AV dissociation, and fusion beats, which are integrated into the VT complex.

VT may develop without hemodynamic deterioration. Nevertheless, it often causes severe hemodynamic compromise and may deteriorate rapidly into VF. Therefore, this tachyarrhythmia also must be addressed swiftly to avoid morbidity or mortality.

VT is defined as three or more beats of ventricular origin in succession at a rate greater than 100 beats per minute. There are no normal-looking QRS complexes. The rhythm is usually regular, but on occasion it may be modestly irregular. The arrhythmia may be either well-tolerated or associated with grave, life-threatening hemodynamic compromise. The hemodynamic consequences of VT depend largely on the presence or absence or myocardial dysfunction (such as might result from ischemia or infarction) and on the rate of VT. AV dissociation usually is present, which means that the sinus node is depolarizing the atria in a normal manner at a rate either equal to, or slower than, the ventricular rate. Thus, sinus P waves sometimes can be recognized between QRS complexes. They bear no fixed relation to the QRS complexes unless the atrial and ventricular rates happen to be equal. Conduction from atria to ventricles is usually prevented because the AV node or ventricular conduction system is refractory due to ventricular depolarizations caused by the VT. VT is uncommon in the absence of apparent heart disease.

Myocardial infarcts heal by forming scar tissue, which can lead to VT. This can occur days, months, or years after the infarction. VT can also result from anti-arrhythmic medications (an undesired effect) or from altered blood chemistries (such as low potassium or magnesium levels), pH (acid-base) changes, or insufficient oxygenation.

Fast atrial arrhythmias such as atrial fibrillation (AF) and atrial tachycardia (AT) are abnormal heart rhythms which afflict around three million people each year in the United States. The most prevalent electrical manifestation of the disease electrically is a preponderance of irregular AF wavelets of activation. These irregular AF wavelets are frequently generated in the pulmonary veins (PVs) and are conducted into the left atrium and then the right atrium, causing chaotic and rapid activation that interferes with the normal sino-atrial and atrio-ventricular (SA/AV) node cardiac electrical pathways and generates rapid, irregular ventricular contractions. These irregular AF wavelets can be in the form of AF or atrial flutters, typical and atypical, which may vary in terms of severity and rate. AF makes the ventricular response so irregular and fast that it interferes with normal blood flow through the heart chambers, can lead to severe structural heart disease, and can be life-threatening if not treated effectively. While the irregular rate of ventricular contraction during AF and AT may compromise cardiac output and cause fatigue, much of the increased mortality associated with AF is due to clot formation resulting from poor circulation in the atria that embolizes to cause stroke, renal infarcts, etc. Persistent AF over weeks or months is particularly dangerous.

A procedure to treat AF or AT is DC cardioversion shock therapy to convert AF/flutter to sinus rhythm. This is an excellent conversion tool; however, unless the underlying cause of the AF is resolved, it most likely will recur. Implantable cardioverter defibrillators (ICDs) have been used for conversion of AF; however, since the patient is conscious when the shock is delivered, many individuals find the discomfort of the shock intolerable.

Modern ICDs operate basically by using a high voltage capacitor discharge which consists of four IGBT or MOSFET saturated switches in an H-bridge configuration which produces biphasic truncated exponential (BTE) waveforms. This consists of a phase 1 positive pulse and a phase 2 negative pulse that makes up the BTE waveform. There are only a few manufacturers of ICDs in the world, and the BTE waveform may vary between brands. However, this would be relative to peak voltage for phase 1, the tilt angle or decay of the capacitor discharge, and the pulse-width variability of phase 1 and phase 2. The anode lead is generally inserted in the RV at the apex or most distal end of the RV heart chamber. The cathode is generally the "Hot Can" which is the ICD case.

The more sophisticated of these technologies sample the impedance as the fast leading edge of phase 1 shock is delivered through the heart. Based on the impedance calculated from the initial phase 1 shock, the microprocessor within the ICD adjusts the phase 1 pulse width which minimizes the tilt or rate of decay or discharge from the capacitors. In other words, in the depolarization phase, total pulse width is adjusted in an attempt to maintain the tilt angle of phase 1 by narrowing the pulse width to maintain as much constant energy delivery as possible.

In phase 2, known as the hyperpolarization phase, the pulse is generated by truncating or fast switching from one pair of IGBTs to the second pair which switches the remaining energy stored in the capacitor(s) negative with respect to the zero voltage crossing point. The remaining energy is delivered and usually presented by an appearance of having approximately one half the peak voltage of phase 1 and is conducting until the manufacturer decides a pre-determined pulse width time period which is adequate for hyper-polarization of the ventricular cardiac syncytium. The appearance will also present a positive tilt angle based on the decay rate of the remaining energy stored within the capacitors. Some stored voltage and energy may be remaining on the capacitor(s). Anode and cathode are swapped electrically when the voltage and current change direction between phase 1 and phase 2.

Different manufacturers have made their own calculations and their own determinations regarding phase 1 and phase 2 peak voltages and time periods.

In sum, the only dynamic, "real time" adjustments that can be made on-the-fly during a cardioversion or defibrillation shock is the ability to (1) measure the impedance of the cardiac muscle, and (2) change the phase 1 and phase 2 pulse widths in an attempt to adjust and hold up the tilt angle, particularly of phase 1, to statistically most effectively and reliably cardiovert and/or defibrillate. BTE waveforms contain a fast leading edge rise time from zero to about +600 VDC to +800 VDC. However, the remainder phase 1 and 2 waveforms are descending in nature, that is, they deliver decreasing energy with increasing time.

All of the conditions described above can be treated by defibrillation, including external defibrillation or cardioversion. There is a need for devices for delivering more appropriate waveform shocks and for improved waveform management systems.

OBJECTS OF THE INVENTION

It is an object of the invention to provide a novel amplifier-based implantable cardio defibrillator (ICD) which uses a transvenous lead wire.

It is also an object of the invention to provide a novel amplifier-based subcutaneous implantable cardio defibrillator (SICD) which uses a subcutaneous lead wire.

It is a further object of the invention to provide a novel method and apparatus for ICD transvenous pacing, anti-tachycardia pacing (ATP), cardioversion, and defibrillation using a single-wire, amplifier-based system.

It is a further object of the invention to provide a novel method and apparatus for ICD transvenous pacing, anti-tachycardia pacing (ATP), cardioversion, and defibrillation using a single-wire, amplifier-based system using ascending arbitrary waveforms.

It is a further object of the invention to provide a novel method and apparatus for SICD cardioversion and defibrillation using a single-wire subcutaneous system.

It is a further object of the invention to provide a novel method and apparatus for SICD cardioversion and defibrillation using a subcutaneous, single-wire, amplifier-based system using ascending arbitrary waveforms.

It is a yet further object of the invention to provide a method and apparatus for a defibrillation waveform energy control system.

It is a yet further object of the invention to provide a method and apparatus for delivering constant voltage, constant current, or constant energy waveforms.

It is a yet further object of the invention where an amplifier-based defibrillation and or cardioversion system can deliver arbitrary waveforms, including ascending ramp, ascending exponential, level, curved or any other waveform for phase 1 and phase 2 which are useful in the science of defibrillation and cardioversion.

It is a yet further object of the invention to provide a method and system where the high voltage shocks employ increasing energy with increasing time waveforms.

It is a yet further object of the invention to provide a method and system wherein arbitrary waveforms and a slower rate of change are employed, such as ascending ramp waveforms, as well as reduced peak voltages resulting in reduced cardiac damage, for defibrillation and cardioversion.

It is a yet further object of the invention to provide a method and system for cardioversion and defibrillation whereby if the first cardioversion or defibrillation shock fails, another shock comprised of different biphasic waveforms may be selected to enhance and capture outlier patients who are difficult to cardiovert or defibrillate, thereby increasing the overall rescue rate for patients that require cardioversion and/or defibrillation.

It is a yet further object of the invention to provide a method and system whereby phase 1 and phase 2 arbitrary waveforms may be mixed and matched to ensure a higher rate of conversion.

It is a yet further object of the invention to provide a method and system for creating phase 2 waveforms whereby the shock voltage may be "hard-switched" negative with respect to the zero voltage crossing point to any specified negative voltage potential.

It is a yet further object of the invention to provide a method and system using narrow phase 2 pulse widths between one and about three milliseconds to hyperpolarize the myocardium after the phase 1 shock has been delivered.

It is a yet further object of the invention to provide a method and system using narrow phase 2 pulse widths of any arbitrary geometry may be employed for phase 2 such as ascending ramp, ascending exponential, level, curved or any other waveform that hyperpolarize the myocardium after the phase 1 shock has been delivered.

These and other objects of the invention will become more apparent from the description and claims below.

SUMMARY OF THE INVENTION

In one aspect of the invention, a method and system are directed to the delivery of unique arbitrary biphasic ascending phase 1 and phase 2 waveforms, cardioversion and defibrillation shocks which employ (1) constant current, (2) constant voltage, or (3) constant energy modes of operation.

In another aspect of the invention, a system uses a waveform control whereby the ascending waveform shocks are delivered using unique ascending phase 1 and phase 2 waveforms, cardioversion and defibrillation shocks which employ (1) constant current, (2) constant voltage, or (3) constant energy modes of operation using software commands to change the total energy within the shock waveform without changing the peak voltage of the waveform. Examples include chopping the ascending waveforms in some portion of (most favorably) phase 1, that is, turning the waveform on and off at a rate which does not affect defibrillation or cardioversion performance, but does reduce energy consumed from the power supply and battery as well as minimizes the power dissipation within the power electronics within an ICD or SICD.

Another aspect of the invention is the formation of ascending curved waveforms with a plateau during the last one to two milliseconds of the ascending waveform whereby changing the curve will change the delivered energy within the waveform and this is performed through software commands that do not change the peak voltage or pulse width, but do change the energy delivered and used.

Another aspect of the invention is directed to use of an amplifier array wherein each amplifier is driven differentially for the purpose of creating high voltage/high current ascending shocks via software commands.

Another aspect of the invention is directed to a method and system for creating phase 2 waveforms whereby the shock voltage is "hard-switched" negative with respect to the zero voltage crossing point to any specified negative voltage potential, and preferably, using narrow pulse widths between one and three milliseconds to hyperpolarize the myocardium after the phase 1 shock has been delivered.

Another aspect of the invention is directed to a method and system for creating phase 2 waveforms whereby the shock voltage is delivered as ascending ramp, chopped, curved square, rectilinear or level arbitrary waveforms that are negative with respect to the zero crossing point to any specified negative voltage potential, and preferably, using narrow pulse widths between one and four milliseconds to hyperpolarize the myocardium after the phase 1 shock has been delivered.

In another aspect of the invention, as documented in AHA Circulation, September 2012, the nature of the ascending defibrillation shock waveforms has been demonstrated to significantly reduce troponin I enzyme levels per shock as compared with the standard biphasic truncated exponential waveforms used in existing ICD technology.

In another embodiment of the invention, a cardiac defibrillation and/or cardioversion waveform energy control system using uses differentially driven amplifier circuit topologies for the purpose of controlling delivered defibrillation and/or cardioversion electrical shocks to convert cardiac arrhythmias that include atrial fibrillation (AF), atrial tachycardia (AT), ventricular fibrillation (VF) or ventricular tachycardia (VT). The biphasic arbitrary shock waveforms deliver increasing energy with increasing time as represented by phase 1 ascending ramp, ascending exponential, ascending chopped, ascending stepped, ascending curved, square, boot-shaped, rectilinear or level and/or any combination of geometric-shaped ascending waveforms. For phase 2, any arbitrary waveform may be employed: ascending negative or descending negative, any pulse-width geometry or tilt may be selected using software commands.

Also, the phase 1 and phase 2 selections may be "hard switched" as a simple capacitive discharge, BTE, or shaped as a perfect rectilinear negative waveform in such a fashion where the drive is operating in a hybrid mode. Any arbitrary waveform may be delivered, and phase 1 may be a completely different waveform than phase 2. The ability to mix and match phase 1 and phase 2 waveforms may be useful in the art and science of cardioversion/defibrillation.

These waveforms may be delivered by selecting one of three amplifier operational modes for software-controlled defibrillation and/or cardioversion shock waveforms which are (1) constant current, (2) constant voltage, or (3) constant energy to manage delivered shock energies by changing the curve and or slope of ascending shocks to control delivered energy without changing peak voltage or phase 1 pulse width of a defibrillation or cardioversion shock.

In another aspect of the invention, an ICD or SICD differentially-driven amplifier system comprises an apparatus for treating VF or VT which employs biphasic shock waveforms which deliver increasing energy with increasing time as represented by phase 1 ascending ramp, ascending exponential, ascending chopped, ascending stepped, ascending curved, square, rectilinear or level and or any combination of geometric shaped ascending waveforms. These may be delivered by any one of the three amplifier operational modes for software-controlled defibrillation and or cardioversion shock waveforms which are (1) constant current, (2) constant voltage, or (3) constant energy for the purpose of controlling delivered defibrillation and or cardioversion electrical shocks to convert cardiac arrhythmias.

In an aspect of the invention, an apparatus is an SICD case or "hot can" installed under the skin on the left chest side in the rib area, and having a lead wire with one or more distal shocking coils which travels between intercostal rib spaces traversing vertically along the left line/edge of the sternum. Shocks are delivered between the hot can and the distal coil electrode(s) for the purpose of defibrillation or cardioversion to change the transmembrane potential in the left and right ventricle sufficiently to convert VF or VT.

In another aspect of the invention, an ICD transvenous differentially-driven amplifier system comprises both a method and apparatus for treating cardiac pacing disorders and defibrillation and/or cardioversion. A single-wire right ventricle pacing lead wire and shocking coil provide primary pacing, ATP, and defibrillation/cardioversion installed within the apex of the right ventricle endocardially. The software-directed system commands the amplifier circuits to provide the selected cardiac pacing, current sensing, ATP, and ventricular defibrillation and or ventricular cardioversion. Conventional pacing/defibrillation ICD systems use a complex insulated combination of isolated pacing wires and defibrillation or cardioversion high voltage shocking lead wire and coil assembly, which are embedded into the apex endocardially in the right ventricle and are prone to leads breaking prematurely.

One-wire ICD defibrillation or cardioversion shocking and transvenous pacing therapy as described herein use amplifier circuits that are capable of delivering high voltage defibrillation and/or cardioversion shocking as well as pacing and ATP therapy, all using one wire. Traditional ICD devices use a separate high voltage shocking wire integrated with an insulated set of pacing and sense wires which deliver the pacing and ATP therapies.

The reason amplifier-based or amplifier technology lends itself well to a one-wire high voltage shock and pacing therapies is that a well designed amplifier using modern day components can reproduce any voltage waveforms or pulses from a microprocessor from microvolts up to about +2000 VDC within one amplifier circuit or two amplifier circuits which are driven differentially, such as an ICD cardiac device. The amplifier ICD transvenous circuits sample the pacing current at the amplifier to make adjustments for capture and deliver the novel concept using ascending or level constant current, constant voltage, or constant energy pacing pulses required by an electrophysiologist to manage bradycardia (unacceptable slow heart rates) as well as deliver anti-tachycardia pacing therapies. In addition, input voltages can be driven at the amplifier input to raise the voltage to very high voltages that are required for defibrillation and or cardioversion.

The advantages and arguments that make a one-wire ICD compelling are that simplicity is achieved through and by using a single amplifier circuit to defibrillate, cardiovert, and/or pace instead of using the traditional independent high voltage circuits and separate pacing and ATP circuits.

Broken lead wires, particularly broken pacing wires, have been a significant problem in terms of patient costs and recall of failed wires involved with ICD lead implants. Using a one-wire shocking and pacing system has great advantages since the high voltage shocking lead is typically more robust than the insulated pacing wires.

The SICD system described herein is not indicated for patients who require anti-bradycardia pacing. The device can deliver pre- and/or post-shock rescue pacing therapy, but in doing so, it also paces the muscle wall, which can be uncomfortable in conscious patients. It can provide anti-tachycardia pacing, which can painlessly terminate ventricular tachycardia, and is designed to treat ventricular arrhythmias at rates lower than 170 bpm. The use of lead anchoring sleeves mitigates the risk of subcutaneous lead migration.

SICDs are as effective as standard transvenous devices in terminating induced ventricular fibrillation, although with higher energy requirements (37J±20J for SICD vs. 11±9J for transvenous ICD); the higher impedance and greater distance from the heart inherent in subcutaneous systems increases the energy requirements approximately three times for successful defibrillation. However, SICDs are not capable of pacing for issues such as bradycardia except at transcutaneous levels, which can be very painful to the patient.

Most patients are more likely to cardiovert/defibrillate with a constant current shock because whatever the chest impedance is adjusting to, this method delivers "constant current," which is specified by the software commands and delivered through the amplifiers. By definition the amplifiers can deliver a constant current into any load impedance by sampling the impedance characteristics of the signal which in this case is an ascending waveform. In the technology described herein, the ideal output waveform is constructed from discrete points in time or equations stored in the microcontroller. At each discrete time point, on the order of microseconds, the microcontroller outputs a new waveform value thru a Digital to Analog converter (DAC) to the amplifiers. At each discrete time point, the current through the load is digitally converted using an Analog to Digital converter (ADC). This digitized current is averaged over multiple time samples to create a rolling average. This rolling current average is used by the microcontroller to calculate power and energy in real time for each discrete time point of the ideal output waveform. The microcontroller then increases or decreases the ideal output waveform to maintain the desired constant current or to achieve the desired total voltage or energy at the completion of the waveform.

Constant current cardioverter/defibrillators that use ascending ramp type waveforms have not been known before. However, they would be most preferred as they will be more predictable in terms of rescue and consistent cardiac conversion.

In another aspect of the invention, a cardiac defibrillation or cardioversion waveform energy control system for treating cardiac arrhythmias in a patient, comprises differentially driven amplifier circuit operational modes to control the delivery of defibrillation or cardioversion electrical shocks, wherein the shock waveforms are constant current, constant voltage, or constant energy.

In another aspect of the invention, in a method for treating cardiac arrhythmias in a patient, a cardiac defibrillation or cardioversion waveform energy control system comprises differentially driven amplifier circuit operational modes to control the delivery of defibrillation or cardioversion electrical shocks, wherein the shock waveforms are constant current, constant voltage, or constant energy.

In another aspect of a system or method of the invention, the cardiac arrhythmias are atrial fibrillation (AF), atrial tachycardia (AT), ventricular fibrillation (VF), or ventricular tachycardia (VT).

In another aspect of a system or method of the invention, biphasic arbitrary shock waveforms deliver increasing energy with increasing time as represented by phase 1 ascending ramp, ascending exponential, ascending chopped, ascending stepped, ascending curved, square, or rectilinear or any combination of geometric shaped ascending or level waveforms.

In another aspect of a system or method of the invention, selection of defibrillation or cardioversion shock waveform modes and delivery of the shocks is software-controlled.

In another aspect of a system or method of the invention, unique arbitrary biphasic ascending phase 1 and phase 2 waveforms are delivered, which arbitrary waveforms deliver increasing energy with increasing time.

In another aspect of the invention, the system is an ICD or an SICD.

In another aspect of the invention, the system is a transvenous ICD, single-wire implantable cardiodefibrillator.

In another aspect of a system or method of the invention, a transvenous single-wire system delivers both the pacing voltages and the defibrillation/-cardioversion shocks within the right ventricle, which simplifies the system and reduces the possibility of broken pacing wires.

In another aspect of the invention, the system is an SICD with a subcutaneously extending lead wire.

In another aspect of the invention, the system or method provides safer, more efficient arbitrary waveforms in a process which delivers increasing energy with increasing time, and thus lower peak voltages and slower rates of change are employed.

In another aspect of the invention, the system comprises class A to Z or any other class of amplifier circuit topology to process arbitrary ascending waveforms that deliver increasing energy with increasing time for a positive phase 1 and negative energy for phase 2 time periods that can range from about 500 ns to about 100 ms pulsed, chopped, stepped, or continuous waveforms using any voltage for phase 1 and phase 2 from about 0 VDC to +/−1500 VDC.

In another aspect of the invention, the system comprises class A to Z or any other class of amplifier in cardioversion or defibrillation transvenous ICD or SICD systems to process arbitrary waveforms that deliver increasing energy with increasing time for a positive phase 1 and negative energy for phase 2 where only the highest power dissipation portion of the waveform is pulsed or chopped to reduce power dissipation in the electronic output circuits and component devices of cardioversion/defibrillation for ICD or SICD systems using software commands.

In another aspect of the invention, the system comprises class A to Z or any other class of amplifier used in cardioversion or defibrillation for transvenous ICD or SICD systems for controlling phase 2 waveforms whereby the waveform is "hard-switched" from the zero voltage crossing point to a negative voltage potential as specified by software commands and as a minimum pulse width from about one to about three milliseconds, and whereby ascending arbitrary waveforms are delivered using lower peak voltages and creating shock vectors that optimize efficiency and safety during defibrillation of VF and VT.

In another aspect of the invention, a system for a dynamic amplifier-based transvenous ICD or SICD system is controlled via software commands and is capable of delivering all known BTE shock waveforms with any tilt angle specified via software in addition to thousands of protocols using ascending waveforms which offer constant energy, constant voltage or constant current modes of operation which are unique and novel to the field.

In another aspect of the invention, in an amplifier-based transvenous ICD or SICD system, any ascending arbitrary waveform within the limits of the stored energy within a transvenous ICD or SICD may be delivered using software commands, enabling this system to maximize the reduction in damage to the heart and have the highest statistical cardioversion and defibrillation rate.

In another aspect of the invention, the amplifier-based ICD or SICD system using software commands can deliver constant current, constant voltage or constant current modes in transvenous ICDs or subcutaneous SICDs.

In another aspect of the invention, the amplifier-based system can be configured using software commands to deliver any ascending phase 1 waveforms and deliver a "hard switched" phase 2 waveform whereby the amplifiers are commanded to operate in a saturated switch mode that can deliver the phase 2 waveform as a fast vertical negative discharge from the remaining energy stored in the capacitor(s) and phase 1 can be an ascending waveform of any geometry and where phase 2 may be switched negative relative to the zero voltage crossing point without any appreciable slope or ramp for the purpose of hyperpolarizing the syncytium of the heart using a narrow rectilinear waveform geometry which is most advantageous to defibrillation or cardioversion whereby this capability allows for a hybrid approach in that any phase 1 ascending or level geometry waveform may be employed in concert with any phase 2 waveform including fast rectilinear or hard switching phase 2 which provides for the ability to mix and match phase 1 and phase 2 waveform geometries giving the cardiologist/EP the most options to select from when treating patients that require a more sophisticated cardioversion/defibrillation shock protocol.

The invention comprises a product possessing the features, properties, and the relation of components which will be exemplified in the product hereinafter described and the scope of the invention will be indicated in the claims.

BRIEF DESCRIPTION OF THE DRAWINGS

For a fuller understanding of the invention, reference is made to the following description taken in connection with the accompanying drawings, in which.

DETAILED DESCRIPTION OF THE DRAWINGS

Figure 1:
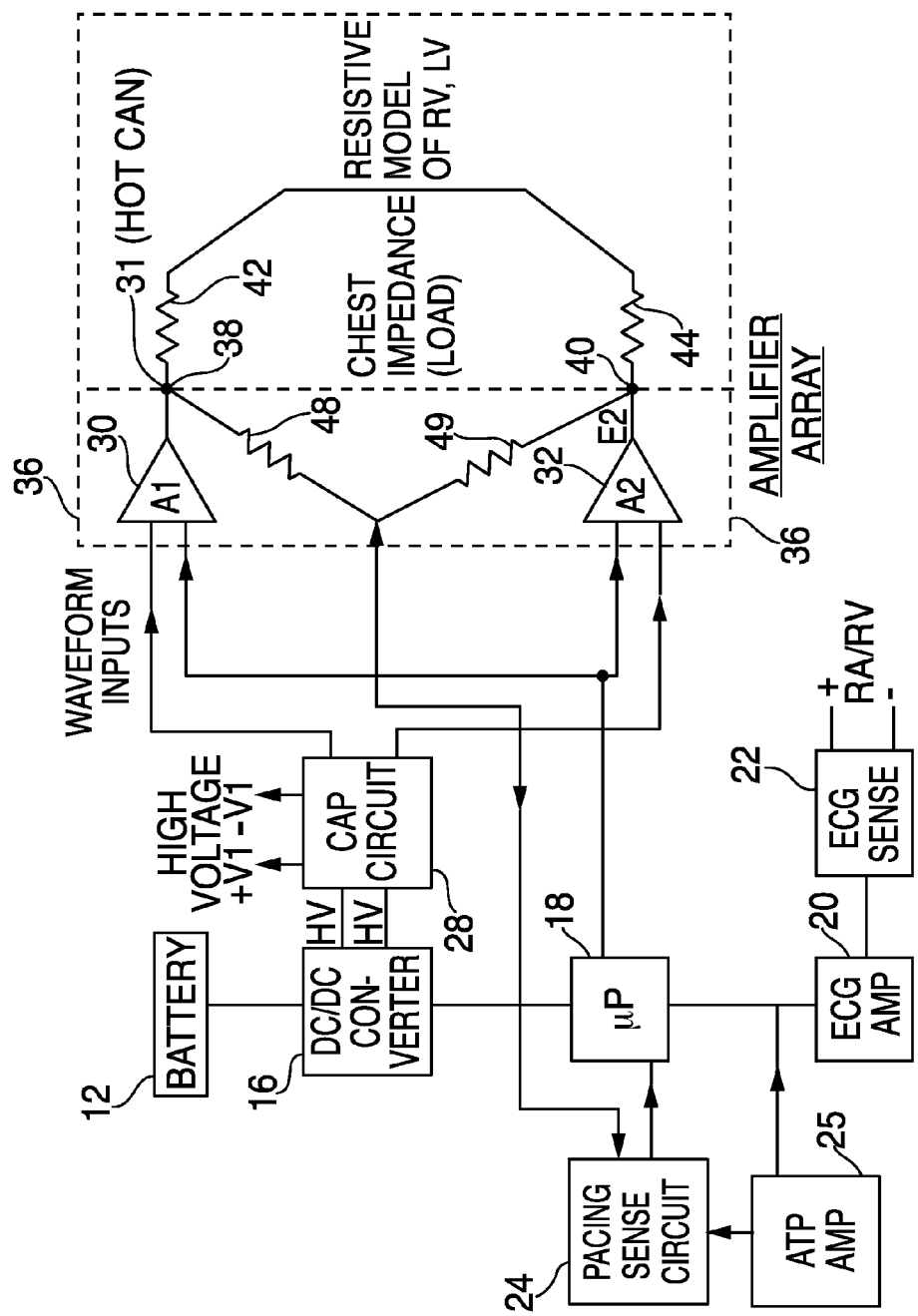
FIG. 1 represents a system diagram of an embodiment of the invention for an ICD.

The system diagram for an ICD represented by FIG. 1 illustrates one embodiment of an amplifier-based defibrillation or cardioversion system useful according to the invention. A battery 12 provides power to a pulse width modulated (PWM) and regulated DC/DC converter 16, which in turn distributes a control voltage to a microprocessor 18, which in turn sends a signal to an ECG Amp 20 and an ECG Sense Analyzer 22. DC/DC converter 16 also distributes high voltage to a capacitor circuit 28 and two amplifiers 30 and 32. A lead wire is implanted within the right ventricle, represented by chest impedance resistors 42, 44. Electrode 40 is a single wire that serves as the single pacing wire or ATP therapy, defibrillation, or cardioversion lead wire. Amplifier 30 and Hot Can 31 serve as electrode 38. Pacing sense circuit 24, ATP Amp 25, and sense resistors 48 and 49 make up the current feedback to microprocessor 18 for the one-wire pacing and ATP functions.

Figure 2:
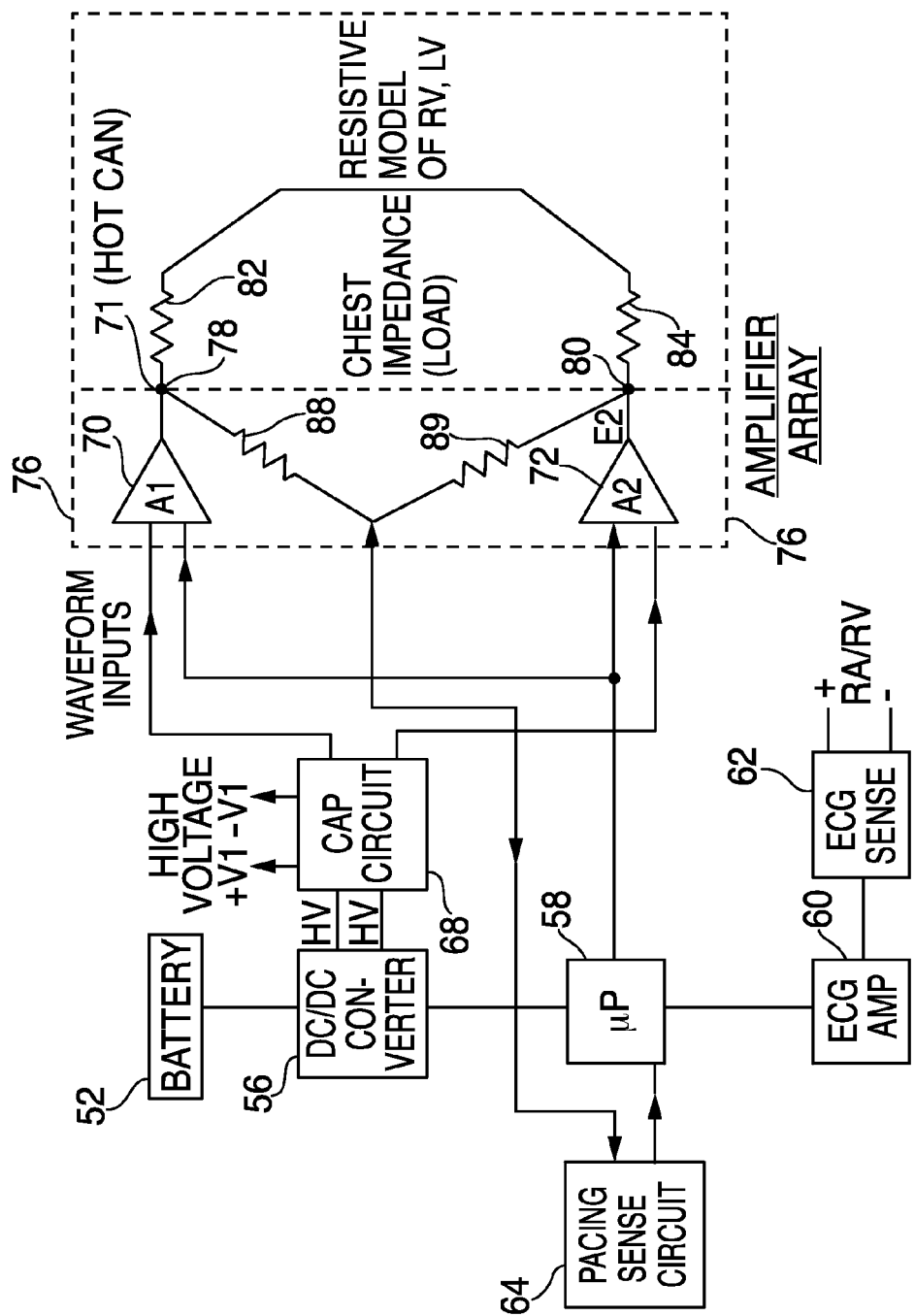
FIG. 2 represents a system diagram of an embodiment of the invention for an SICD.
Figure 3:
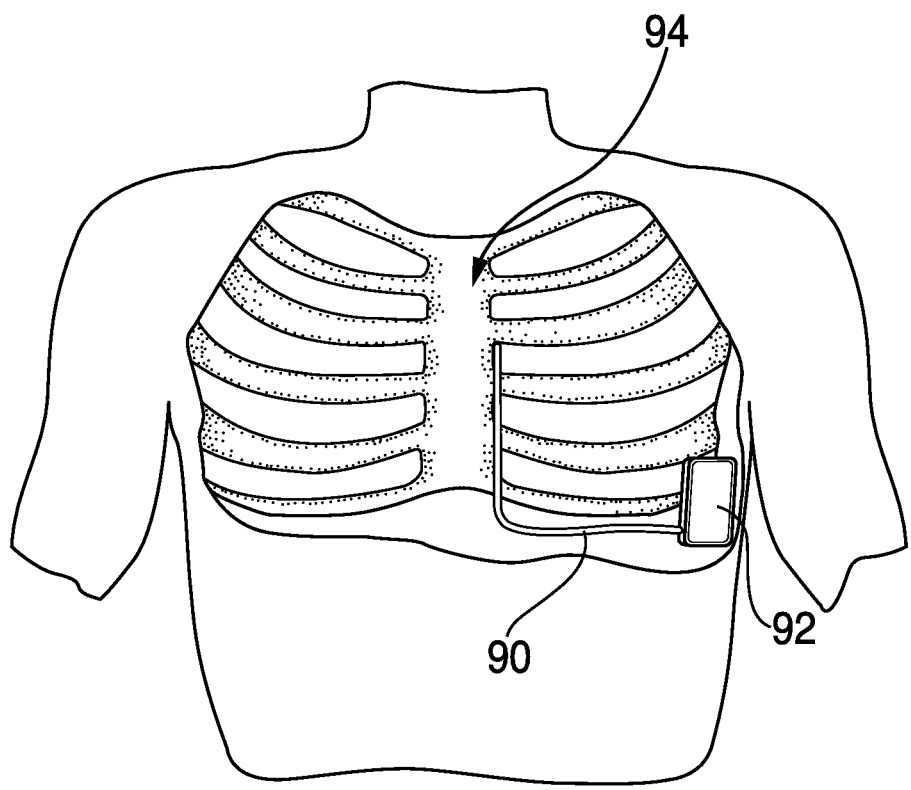
FIG. 3 is a representation showing placement of an amplifier-based SICD according to the invention.

The system diagram for an SICD represented by FIG. 2 illustrates one embodiment of an amplifier-based defibrillation system useful according to the invention. A battery 52 provides power to a pulse width modulated (PWM) and regulated DC/DC converter 56, which in turn distributes a control voltage to a microprocessor 58, which in turn sends a signal to an ECG Amp 60 and an ECG Sense Analyzer 62. DC/DC converter 56 also distributes high voltage to a capacitor circuit 68 and two amplifiers 70 and 72. Ventricle Electrode 80 with a single wire serves as the single defibrillation or cardioversion wire. The apparatus is an SICD case or "hot can" 71 installed under the skin on the left chest side in the rib area, and having a lead wire with one or more shocking coils which travels between intercostal rib spaces traversing vertically along the left line/edge of the sternum, as shown in FIG. 3. Shocks are delivered between the hot can 92 and the distal coil electrode(s) 90 installed in a patient's chest area 94 for the purpose of defibrillation and/or cardioversion to change the transmembrane potential in the left and right ventricle sufficiently to convert VF or VT. Pacing sense circuit 64 and sense resistors 82 and 84 make up the current feedback to the microprocessor 58 for the one wire pre- and/or post-shock rescue pacing and therapies.

Figure 4:
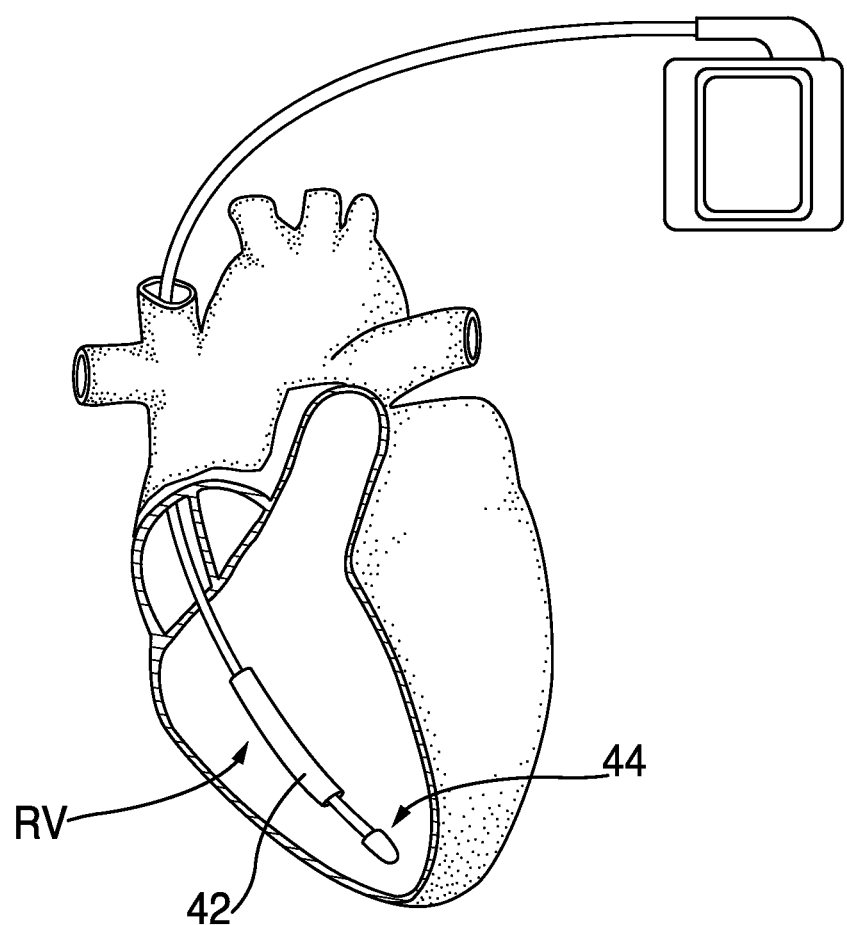
FIG. 4 is a representation showing placement of a transvenous ICD and a single RV transvenous pacing lead and shocking coil as a one-wire defibrillation cardioversion system according to the invention.

In FIG. 4, a single RV pacing lead and shocking coil as a one wire 42 is embedded within the right ventricle apex 44 defibrillation cardioversion system, consistent with FIG. 1. If necessary, energy is delivered to the right ventricle to help it contract normally.

Figure 5A:
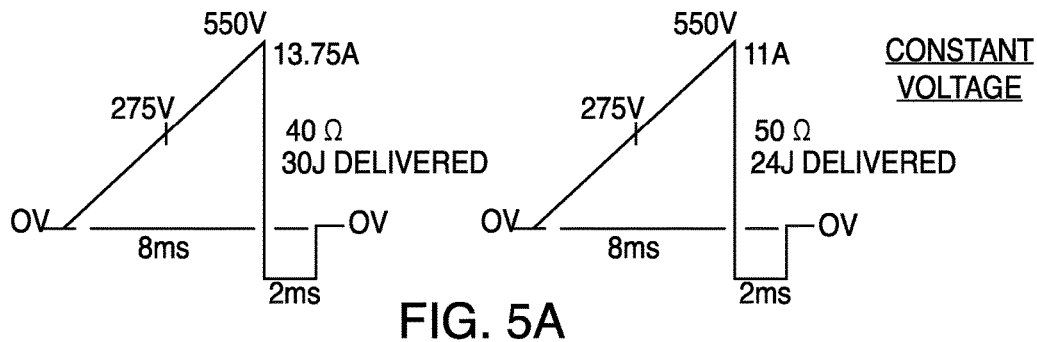
FIGS. 5A to 5C represent examples of amplifier-generated ascending ramp shock waveforms delivered with constant voltage, constant current, and constant energy modes of operation, respectively, wherein impedance, voltage, current, and energy in Joules are delivered in each example shown.
Figure 5B:
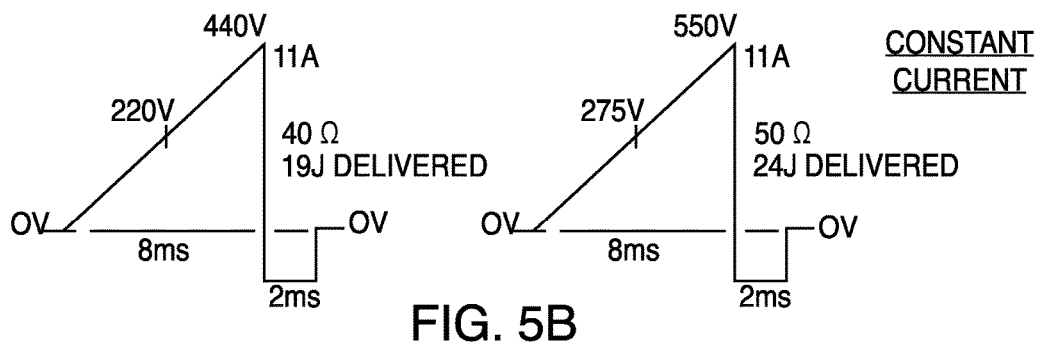
Figure 5C:
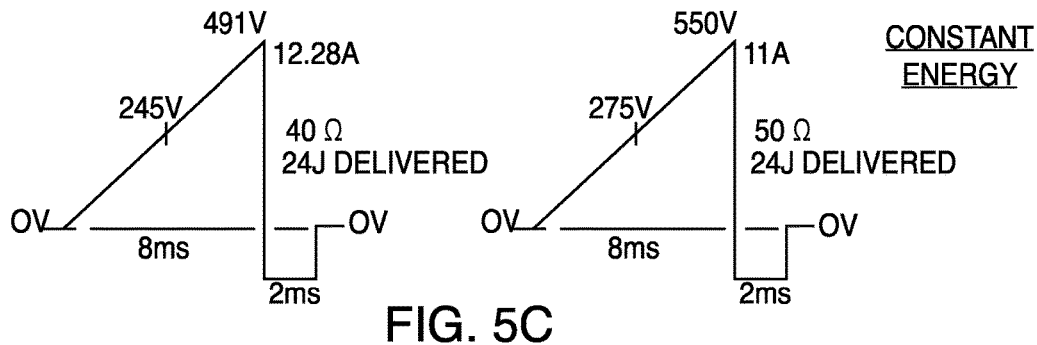

FIGS. 5A to 5C represent amplifier-generated ascending ramp shock waveform examples delivered with constant voltage, constant current, and constant energy modes of operation, respectively. Impedance, voltage and currents delivered in examples are shown.

Figure 6:
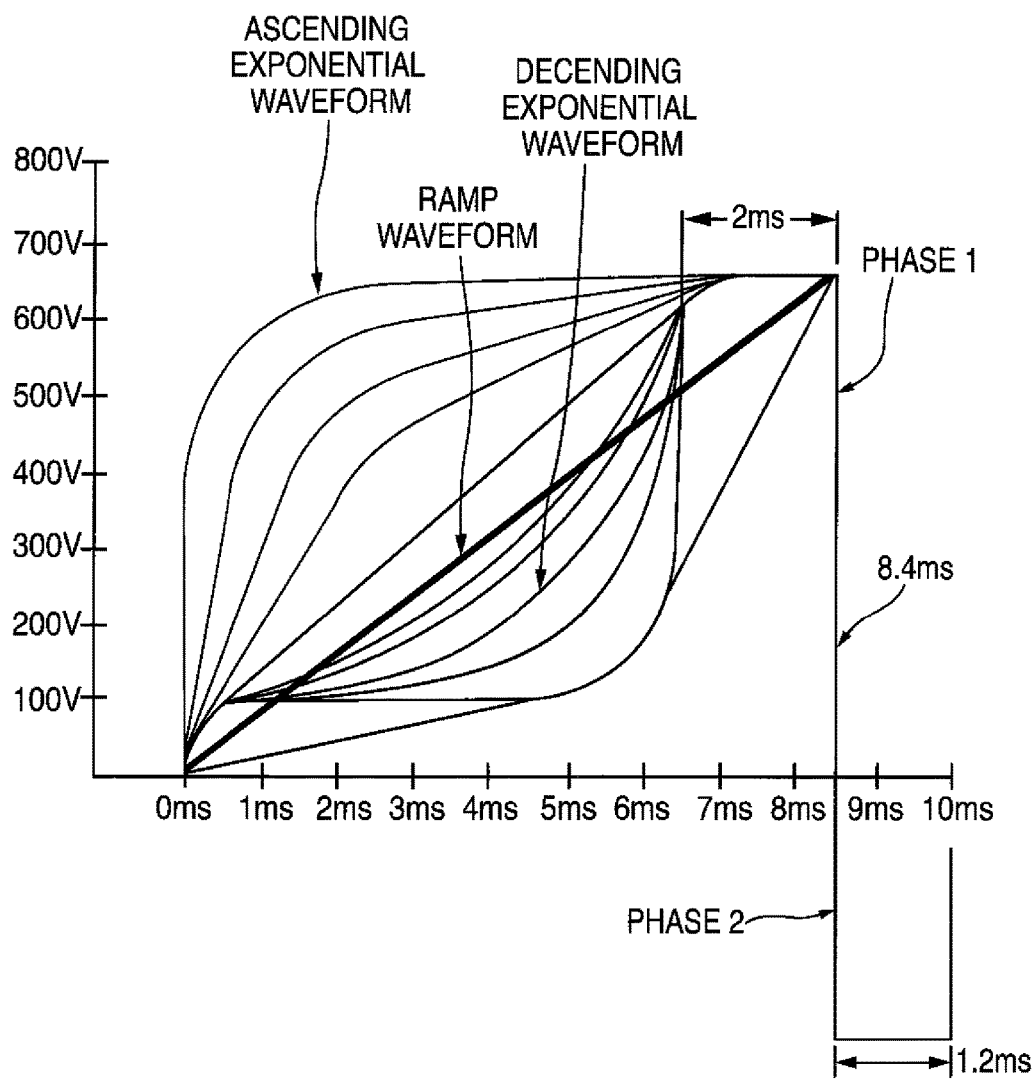
FIG. 6 is a representation of ramp and variable exponential curve waveforms for energy management, according to the invention.

In FIG. 6, ramp and variable exponential curve waveforms for energy management are shown.

Figure 7:
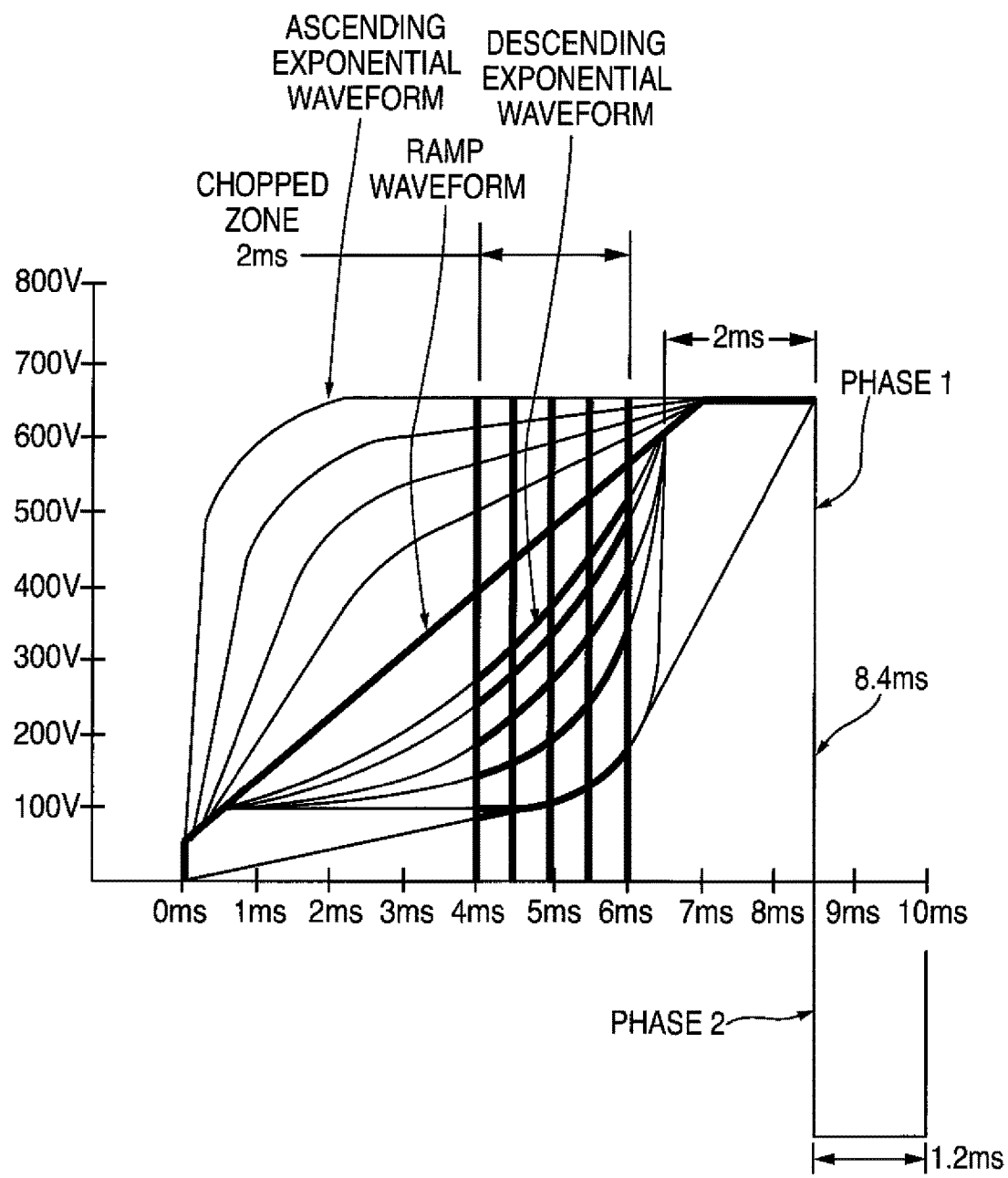
FIG. 7 is a representation of ramp and variable curve ascending exponential curve waveforms with reduced power dissipation chopped ascending waveforms for energy management, according to the invention.

In FIG. 7, ramp and variable curve ascending exponential curve waveforms with reduced power dissipation chopped ascending waveforms for energy management are shown.

Figure 8:
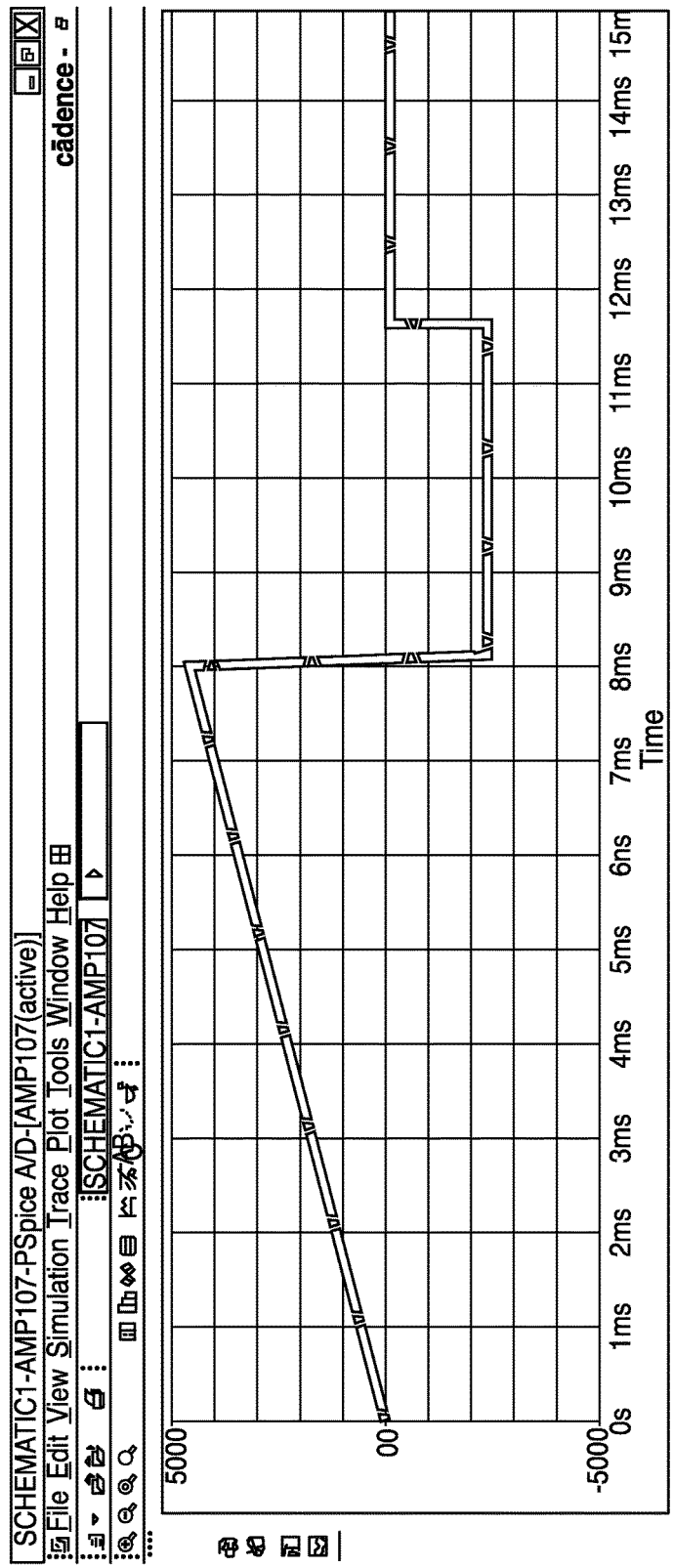
FIGS. 8 and 9 are copies of waveform scope tracings published in *AHA Circulation*, Sep. 11, 2012.

FIG. 8 represents an actual ascending ramp waveform scope tracing published in AHA *Circulation*, Sep. 11, 2012. The ascending ramp DFT was 15J for 8 ms phase 1, and the rectilinear phase 2 was 4J for 3.5 ms phase 2.

Figure 9:
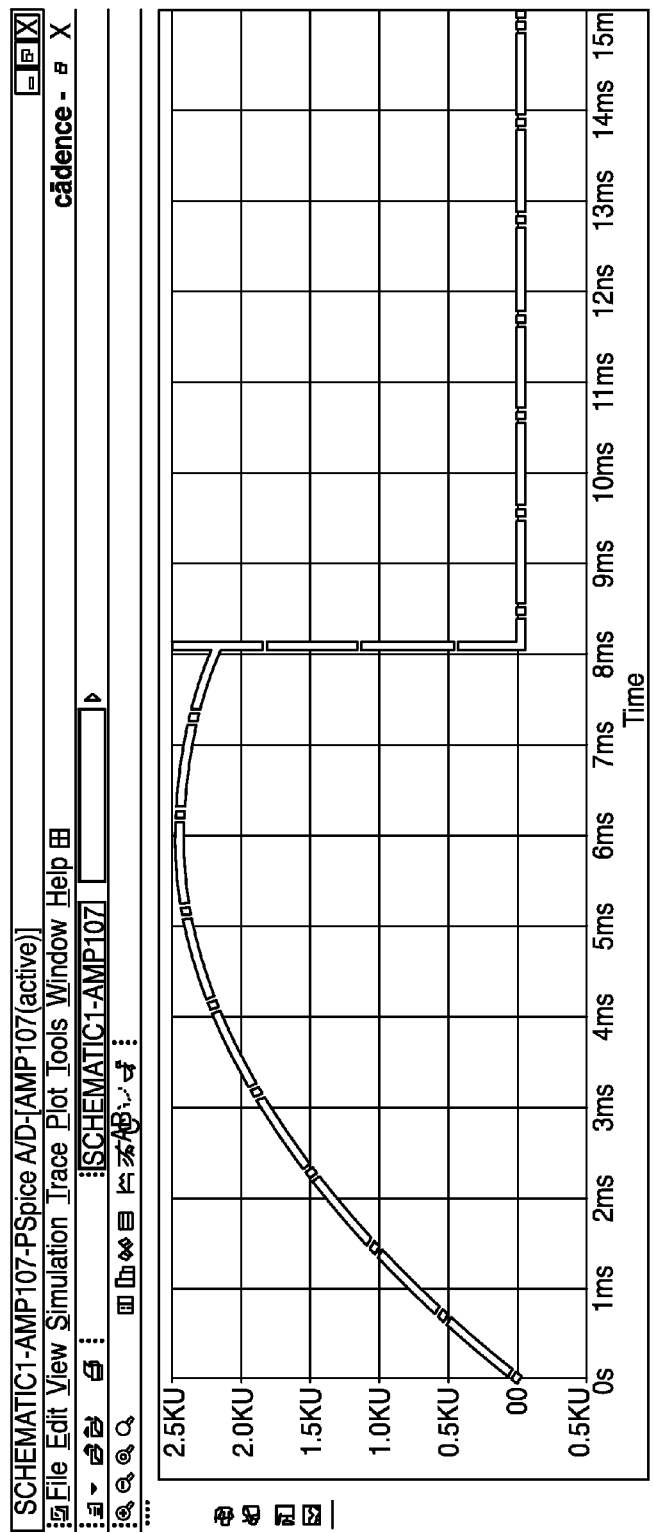

FIG. 9 represents an actual ascending ramp "power band" waveform scope tracing published in AHA *Circulation*, Sep. 11, 2012. The phase 1 power dissipation in power output devices is 13.5 J. The shape of the power band for an ascending ramp waveform should be noted.

Figure 10:
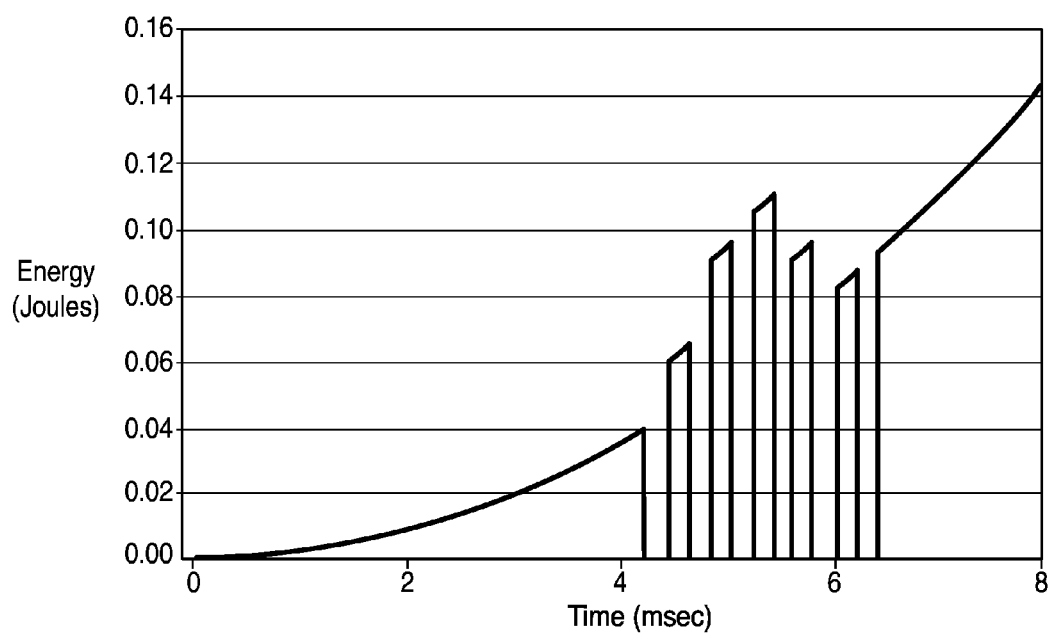
FIGS. 10 to 12 each represent a waveform for power dissipation energy management control system, according to the invention.

FIG. 10 represents an ascending exponential ramp positive chopped portion half way up the ramp for a power dissipation energy management control system. It is also characterized as an ascending ramp software burst control in output devices and into the heart.

Figure 11:
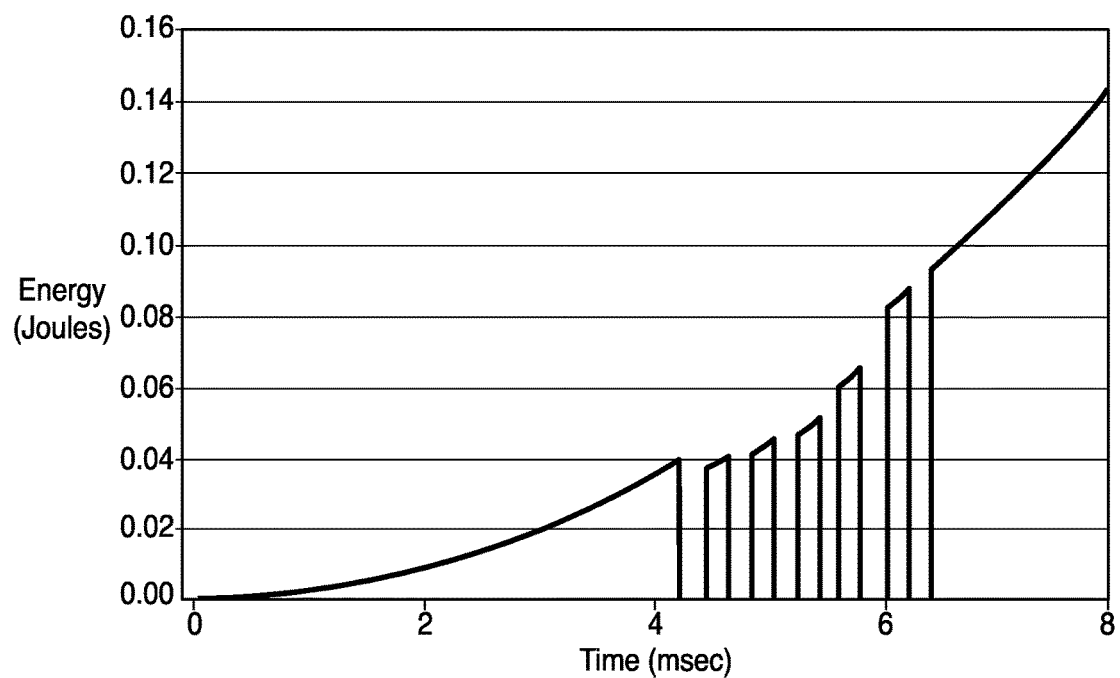

FIG. 11 represents an ascending exponential ramp negative curved chopped portion half way up the ramp for a power dissipation energy management control system. It is also characterized as an ascending ramp software burst control in output devices and into the heart.

Figure 12:
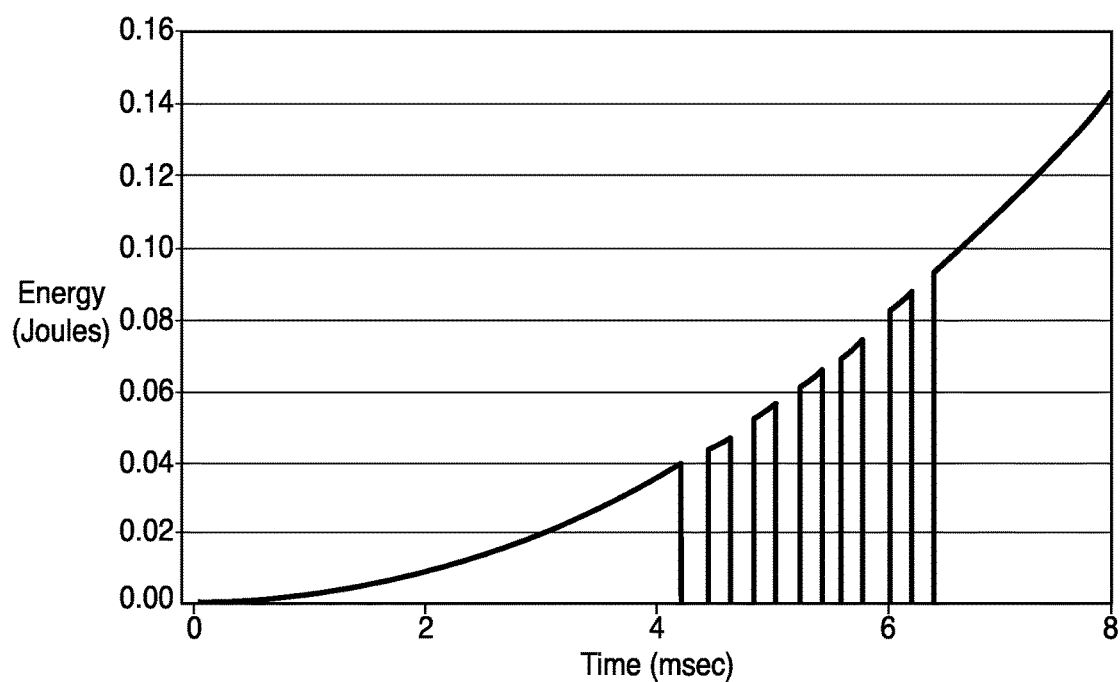

FIG. 12 represents an ascending exponential ramp equal curve chopped half way up the ramp for a power dissipation energy management control system. It is also characterized as an ascending ramp 50% pulsed waveform.

It will thus be seen that the objects set forth above, among those made apparent from the preceding description are efficiently attained and, since certain changes may be made in the devices and methods set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention, which, as a matter of language, may be said to fall there between.

We claim:

1. A waveform energy control system for treating a cardiac condition in a patient, which comprises:
   a microcontroller;
   a digital-to-analog converter (DAC); and
   differentially driven amplifier circuits having an input and an output,
   wherein the microcontroller is operatively connected to the DAC, the DAC is operatively connected to the input of the differentially driven amplifier circuits, the microcontroller is configured to respond to software commands to generate signals to the DAC, the DAC provides signals to the input of the differentially driven amplifier circuits, and the output of the differentially driven amplifier circuits delivers constant current, constant voltage, or constant energy ascending arbitrary waveforms, biphasic truncated exponential (BTE) waveforms, or ascending arbitrary and BTE waveforms for pacing, anti-tachycardia pacing (ATP), low-voltage therapy, defibrillation, or cardioversion electrical shocks to the patient's heart.

2. The waveform energy control system of claim 1, wherein the cardiac condition treated is atrial fibrillation (AF), atrial tachycardia (AT), ventricular fibrillation (VF), or ventricular tachycardia (VT).

3. The waveform energy control system of claim 1, wherein the waveforms produced are biphasic waveforms comprising a first phase (phase 1) having a positive voltage potential with respect to a zero voltage crossing point in the form of an ascending ramp, ascending exponential, ascending chopped, ascending stepped, ascending curved, square, rectilinear, BTE, or any combination of geometric-shaped waveforms, followed by a second phase (phase 2) having a negative voltage potential with respect to a zero voltage crossing point in the form of an ascending ramp, ascending exponential, ascending chopped, ascending stepped, ascending curved, square, rectilinear, BTE, or any combination of geometric-shaped waveforms, to deliver increasing energy with increasing time.

4. The waveform energy control system of claim 3, wherein the phase 1 or phase 2 defibrillation or cardioversion shock waveforms are produced in response to software commands programmed in the microcontroller.

5. The waveform energy control system of claim 3, wherein shock waveforms are applied internally through a patient's heart and chest and an output waveform is constructed from discrete points in time or equations stored in the microcontroller which at each discrete time point, on the order of microseconds, the microcontroller outputs a new waveform value through the DAC to the amplifiers and at each discrete time point, the current through the patient's heart and chest is converted using an analog-to-digital converter (ADC) wherein a digitized current generated from sense resistors provides electronic feedback to the microcontroller and is sampled at multiple intervals, creating a rolling current average used by the microcontroller and software to calculate power, energy, and voltage in real time for each discrete time point of the output waveform in which the microcontroller then increases or decreases the output waveform to maintain the desired constant current, constant energy, or constant voltage.

6. The waveform energy control system of claim 3, wherein the differentially driven amplifier circuits provide arbitrary ascending waveforms, BTE waveforms, or ascending and BTE waveforms with positive voltage and energy for phase 1 and negative voltage and energy for phase 2 time periods that can range from about 500 ns to about 100 ms configured as ramp, curved, stepped, BTE, or continuous waveforms using any voltage for phase 1 and phase 2 from about 0 VDC to +/−1500 VDC.

7. An implantable cardiac defibrillator system, which comprises:
   a subcutaneous case capable of being positioned under a patient's skin in the pectoral area of the patient's upper left chest;
   the waveform energy control system of claim 1 located within the subcutaneous case; and a single lead wire transvenously extending from the subcutaneous case and capable of being installed in the patient's right ventricle for pacing, anti-tachycardia pacing (ATP), low-voltage therapy, cardioversion, or defibrillation.

8. The implantable cardiac defibrillator system of claim 7, wherein increasing energy with increasing time is delivered for a positive energy phase of the waveforms and a negative energy phase of the waveforms where only the highest power dissipation portion of a waveform is pulsed or chopped to minimize power dissipation in the output circuits.

9. The implantable cardiac defibrillator system of claim 7 which is capable of delivering BTE shock waveforms with a tilt angle and waveform pulse width specified via software commands to provide a constant energy, constant voltage, or constant current mode of operation.

10. The implantable cardiac defibrillator system of claim 7, wherein, if a shock for defibrillation or cardioversion fails, one or more subsequent shocks or low voltage therapy may be delivered for defibrillation or cardioversion using any arbitrary ascending waveform or BTE waveform saved in the microcontroller memory.

11. A subcutaneous implantable cardiac defibrillator system (SICD), which comprises:
   a subcutaneous case capable of being positioned under a patient's skin on the left side of a patient's rib cage;
   the energy control system of claim 1 located within the subcutaneous case; and
   a lead wire extending from the subcutaneous case and capable of being positioned subcutaneously above or below the patient's sternum for pacing, ATP, low voltage therapy, cardioversion, or defibrillation.

12. The subcutaneous implantable cardiac defibrillator system of claim 11, wherein increasing energy with increasing time is delivered for a positive energy phase of the waveforms and a negative energy phase of the waveforms where only the highest power dissipation portion of a waveform is pulsed or chopped to minimize power dissipation in the output circuits.

13. The subcutaneous implantable cardiac defibrillator system of claim 11, wherein the SICD system is controlled via software commands and delivers BTE shock waveforms with a tilt angle and waveform pulse width specified via said software commands to provide a constant current, constant voltage, or constant energy mode of operation.

14. The subcutaneous implantable cardiac defibrillator system of claim 11, wherein, if a first shock for defibrillation or cardioversion fails, one or more subsequent shocks or low voltage therapy for defibrillation or cardioversion may be delivered using an arbitrary ascending waveform or BTE waveform saved in the microcontroller memory.

15. An implantable cardiac pacing system, which comprises:
   a subcutaneous case capable of being positioned under a patient's skin in the pectoral area of the patient's upper left chest;
   the energy control system of claim 1 located within the subcutaneous case; and
   a lead wire transvenously extending from the subcutaneous case and capable of being installed in the patient's right ventricle for pacing, anti-tachycardia pacing (ATP), or low voltage therapy employing ascending arbitrary waveforms or level waveforms.

* * * * *